(12) United States Patent
Webler

(10) Patent No.: US 7,762,958 B1
(45) Date of Patent: Jul. 27, 2010

(54) METHOD AND APPARATUS FOR DETERMINING INJECTION DEPTH AND TISSUE TYPE

(75) Inventor: William Earl Webler, Escondido, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 705 days.

(21) Appl. No.: 10/027,877

(22) Filed: Dec. 19, 2001

(51) Int. Cl.
*A61B 5/00* (2006.01)

(52) U.S. Cl. ...................................... 600/549

(58) Field of Classification Search ................ 600/546, 600/549, 587
See application file for complete search history.

(56) References Cited

U.S. PATENT DOCUMENTS

| | | | |
|---|---|---|---|
| 3,470,604 A * | 10/1969 | Zenick | 29/447 |
| 4,630,477 A | 12/1986 | Murtland, Jr. | |
| 5,207,227 A * | 5/1993 | Powers | 600/504 |
| 5,493,906 A * | 2/1996 | Sen-Zhi | 73/204.15 |
| 5,873,835 A * | 2/1999 | Hastings et al. | 600/488 |
| 6,063,085 A * | 5/2000 | Tay et al. | 606/50 |
| 6,071,281 A | 6/2000 | Burnside et al. | |
| 6,110,183 A * | 8/2000 | Cope | 606/139 |
| 6,120,496 A | 9/2000 | Whayne et al. | |
| 6,142,994 A | 11/2000 | Swanson et al. | |
| 6,152,920 A | 11/2000 | Thompson et al. | |
| 6,431,010 B1 * | 8/2002 | Joffe | 73/861 |
| 6,539,792 B2 * | 4/2003 | Lull et al. | 73/204.15 |

OTHER PUBLICATIONS

Gibbs, 1933. "A Thermoelectric Blood Flow Recorder in the Form of a Needle". Proceedings/Society for Experimental Biology and Medicine. 141-146.*

* cited by examiner

*Primary Examiner*—Max Hindenburg
*Assistant Examiner*—Jonathan M Foreman
(74) *Attorney, Agent, or Firm*—Blakely Sokoloff Taylor & Zafman LLP

(57) ABSTRACT

A method and apparatus are disclosed for determining injection depth and/or tissue type based on the heat dissipation characteristics of body tissue.

27 Claims, 3 Drawing Sheets

METHOD AND APPARATUS FOR DETERMINING INJECTION DEPTH AND TISSUE TYPE

FIELD OF THE INVENTION

This invention relates generally to injection devices, and more particularly to injection devices guided by heat dissipation characteristics of the body tissue through which the device is being inserted.

BACKGROUND

It is increasingly important that a physician or surgeon delivering substances, such as drugs, is able to efficiently and accurately locate the desired target tissue for effective delivery of the substance. This is particularly true when the concentration of the substance required at the target site cannot be safely or effectively achieved by introduction of the substance to a location remote from the target site. Currently, it is difficult to determine injection depth and/or tissue type without visually guiding the needle of an injection device or having some other indication of the needle location within a patient's body.

For example, fluoroscopy can be used to guide the injection device, but fluoroscopy lacks the resolution and sensitivity needed to accurately guide the injection device into the desired tissue location. Alternatively, electrocardiograph signals have been used when delivering substances to ventricular tissues of the heart, but this technique cannot be used throughout the entire body. In addition, the use of imaging systems (e.g., ultrasonic, magnetic resonance, and optical) to view the injection device and surrounding tissue has been proposed, but the barriers to usage of such systems are large (e.g., including large capital investment, large space requirements, and ownership of intellectual property by others).

SUMMARY

A method and apparatus are disclosed for determining injection depth and/or tissue type based on the heat dissipation characteristics of body tissue. In various embodiments, an elongate member such as a needle has at least one thermally conductive heating element mounted thereon. The heating element comprises material whose electrical resistance changes in response to a change in temperature. In addition, the apparatus includes an anemometry circuitry interface electrically coupled to the heating element so that the anemometry circuitry can measure the heat dissipation characteristics of the tissue environment in which the heating element is disposed.

DESCRIPTION OF THE DRAWINGS

Various embodiments are illustrated by way of example and not by way of limitation in the figures of the accompanying drawings in which like references indicate similar elements. It should be noted that references to "an", "one", or "various" embodiments in this disclosure are not necessarily to the same embodiment, and such references mean at least one.

DETAILED DESCRIPTION

The various embodiments described herein use heat dissipation characteristics of tissue to determine injection depth and/or tissue type. In the following description, for purposes of explanation, numerous specific details are set forth in order to provide a thorough understanding of the various embodiments. It will be apparent, however, to one skilled in the art that the various embodiments may be practiced without some of these specific details. The following description and the accompanying drawings provide examples for the purposes of illustration only. However, these examples should not be construed in a limiting sense as they are merely intended to provide exemplary embodiments, rather than to provide an exhaustive list of all possible implementations.

Figure 1:
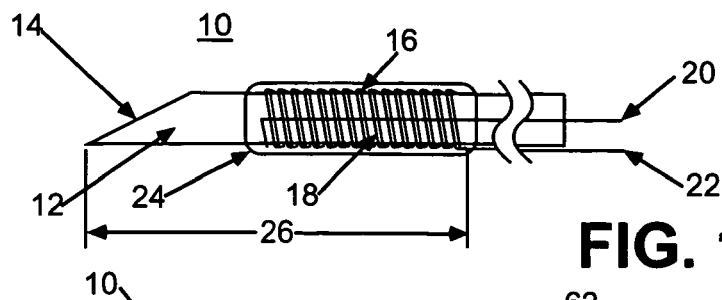
FIG. 1 is an embodiment of a heating element coupled to a needle.

Referring now to FIG. 1, device 10 is shown which comprises cylindrical needle 12 having a lumen therethrough with opening 14 at a distal end to access a desired area within the body. Among other functions, needle 12 can be used to deliver a substance, extract a substance, or otherwise used to puncture tissue. Examples of substances that may be delivered include drugs, pharmaceutical agents, fluids, proteins, polypeptides, gene therapy material, cell therapy material, and deoxyribonucleic acid ("DNA").

The dimensions of needle 12 will vary depending on the application. For instance, needle 12 can be designed for use with an intracardiac catheter to access a patient's atria or ventricles of the heart via a patient's vascular system, for use with an intravascular catheter to access a patient's vascular system, for percutaneous use (e.g., puncturing the skin), and for generally accessing blood-filled cavities and vessels (e.g., blood volumes).

Specifically, if needle 12 is to be used with an intracardiac catheter, the outer diameter of needle 12 is preferably between 0.065 inches (16 gage) and 0.013 inches (29 gage). In this regard, the gage sizes of hypodermic needle stock are relatively standard in the industry and refer to the outer diameter of the needle. The inner diameter will vary depending on the wall type. For intravascular catheter use, needle 12 will preferably have an outer diameter between 0.032 inches (21 gage) and 0.010 inches (31 gage). For percutaneous use, needle 12 can be any size suitable for a particular insertion location and the type of material to be injected or withdrawn. However, the most useful size range of needle 12 for percutaneous use would have an outer diameter between 0.134 inches (10 gage) and 0.009 inches (32 gage). Despite the given size ranges for each application, it is contemplated that sizes outside of the given ranges can be used.

In addition, device 10 includes heating element 16 coupled to an exterior portion of needle 12. Heating element 16 will have approximately the same diameter size constraints as needle 12 listed above for each application. This is due to the fact that a heating element which has an outer diameter substantially larger than the outer diameter of the needle could create problems when inserting and extracting device 10.

Regarding the length of heating element 16, it is preferred that the length be between 0.010 inches and 0.400 inches. However, lengths outside of this range could also be used.

In various embodiments, heating element 16 comprises material whose electrical resistance changes in response to a change in temperature. Specifically, heating element 16 is constructed with a controlled temperature/resistance relationship. In various embodiments, heating element 16 is constructed of tungsten or platinum wire or a thin metallic film. These materials have a resistance which increases as the temperature increases. However, heating element 16 may be constructed of other materials such as those used in thermistors and other devices that exhibit changes in electrical resistance in response to a change in temperature.

Device 10 additionally includes first electrically conductive lead 20 electrically coupled to a first end of heating element 16 and second electrically conductive lead 22 electrically coupled to a second end of heating element 16 to serve as an interface with anemometry circuitry. In other embodiments, an alternative anemometry circuitry interface could be used. Although anemometry circuits are generally used to measure flow rates of fluids, the various embodiments disclosed herein use anemometry circuitry to measure heat dissipation (e.g., flow of thermal energy) from heating element 16.

Although the embodiment shown utilizes cylindrical needle 12 to mount heating element 16, other embodiments contemplate other elongate members (that may be non-cylindrical) so long as they are suitable for insertion into a body. For example, the elongate member could be a thin rod (with or without opening 14 and with or without a sharpened distal end). Furthermore, opening 14, if present, could be disposed more proximally on needle 12, which would allow for heating element 16 to be disposed distal to opening 14. Such a configuration would advantageously provide for heat dissipation measurement in situations in which tissue just distal of the desired injection depth provides a more reliable or larger signal change/reading.

FIG. 1 depicts heating element 16 as a wire. The wire should be large enough to conduct a sufficient amount of current but small enough to be effectively mounted on needle 12. It is worth noting that in various embodiments, heating element 16 can comprise at least one of a wire, a film, and a thermistor material.

In one embodiment, heating element 16 has a length that is approximately equal to or less than the known thickness of a targeted tissue (accounting for the tissue penetration angle of device 10) whose heat dissipation characteristics are to be measured by device 10. Embodiments which include this feature are able to more discretely measure heat dissipation characteristics and detect differences in such characteristics than embodiments with heating elements 16 which are longer and, therefore, have no penetration depth at which heating element 16 is surrounded by only the targeted tissue.

In the embodiment shown in FIG. 1, heating element 16 is shown having a coil portion 18 wrapped around needle 12 with covering 24 disposed over coil portion 18. Covering 24 is adhered to needle 12 or formed as an integral part of needle 12. Covering 24 protects heating element 16 and provides for a smooth transition with the surface of needle 12 to make insertion of needle 12 into tissue easier and less traumatic.

Covering 24 can be made of a non-conductive material to insulate the patient from electrical current flowing through coil portion 18. Moreover, the wire that forms coil portion 18 may also be coated with an electrical insulator. Thus, either or both methods of providing electrical insulation described herein may be used.

FIG. 1 shows heating element 16 as a coiled wire. Other wire configurations are also suitable. For example, heating element 16 can be formed by placing the center of the wire near the distal end of heating element 16 and winding each end 20 and 22 in opposite directions around needle 12 towards the proximal end of needle 12. Alternatively, the wire may be wound in a zigzag pattern, proximally and distally, back and forth in a desired area. Alternatively, heating element 16 can be formed by mounting the wire within a groove or a plurality of grooves formed within the surface of needle 12.

In addition to wire configurations, heating element 16 can be formed by sputtering a thin film of metal over a masked insulator (masked to lay down the desired heating element metal configuration), removing the mask, attaching the conductors, and coating the remaining metal connections with an insulator (e.g., a dielectric material). Moreover, a photo-etching process, similar to that used in the microelectronics industry, could be used to remove metal from needle 12 in the desired configuration.

Heating element 16 can be mounted on needle 12 such that distance 26 (from the distal end of opening 14 to the proximal end of heating element 16) is substantially equivalent to a desired injection depth. Heating element 16 may be enclosed or mounted on or in a suitable assembly, syringe, or catheter to aid in the insertion, advancement, orientation, and delivery of device 10 to the desired position within the body prior to injection.

In addition, the proximal end of device 10 may be provided with suitable electrical connections to external circuitry and/or instrumentation (not shown) as well as fluid connections to force the injectant through device 10. Common catheter assemblies provide such connections.

In various embodiments, needle 12 can be comprised of material which is not electrically conductive (e.g., ceramic) or material which is electrically conductive (e.g., stainless steel). It is worth noting that ceramic needles advantageously increase response time and sensitivity of heating element 16 due to the reduced thermal mass and thermal conductivity of ceramic. However, electrically conductive materials have electrical connection advantages, which can simplify device design. For instance, in embodiments in which a portion of needle 12 is electrically conductive, heating element 16 can be connected to anemometry circuitry by (i) first electrically conductive lead 20 electrically coupled to a first end of heating element 16 and (ii) a conductive portion of needle 12 coupled to a second end of heating element 16.

If a high thermal mass needle (e.g., stainless steel) is used, a thermal insulator can be disposed between heating element 16 and needle 12 to minimize any reduction in response time and sensitivity of heating element 16 caused by needle 12.

Regardless of the construction and materials used to construct heating element 16, device 10 can have more than just a single heating element 16, as shown in FIG. 1. For instance, if a plurality of heating elements 16 are mounted on needle 12 and operated separately and/or in groups, multiple penetration depths/tissue types can be controlled/identified. In addition, a single penetration depth can be more effectively controlled with an embodiment which utilizes a plurality of heating elements 16.

Figure 2:
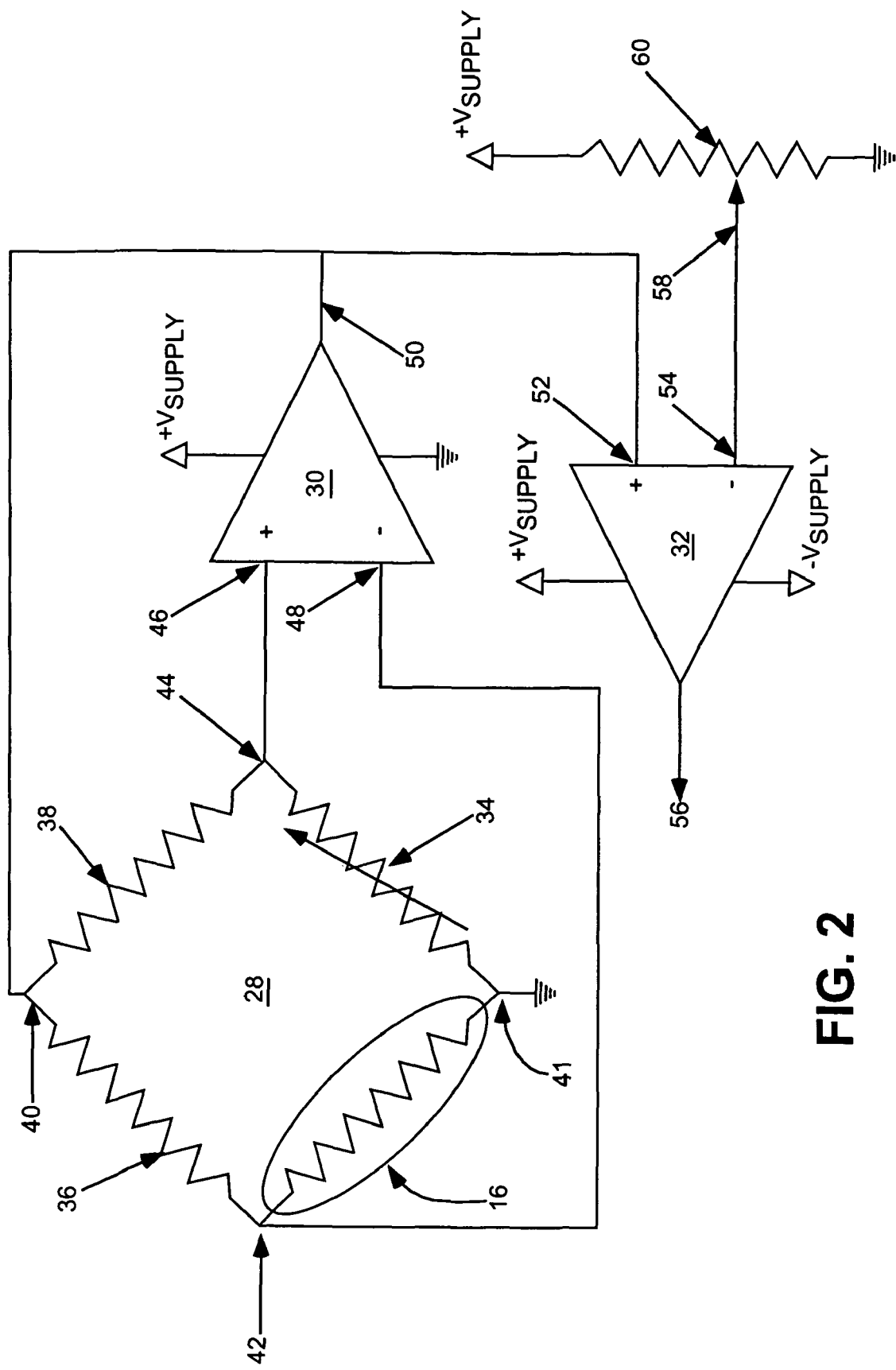
FIG. 2 is an electrical schematic of anemometry circuitry according to an embodiment.

Turning now to FIG. 2, an embodiment of anemometry circuitry is shown. In the embodiment shown, the anemometry circuitry is configured to measure the heat dissipation characteristics of an environment in which heating element 16 is disposed. The anemometry circuitry is electrically coupled to heating element 16 shown in FIG. 1. Specifically, a first end of heating element 16 is electrically coupled to first junction 42 of bridge circuit 28, and a second end of heating element 16 is electrically coupled to node 41 of bridge circuit 28.

FIG. 2 is a simplified representation of a temperature controlled hot wire or hot film anemometer system. Although there are many ways to operate an anemometer system (e.g., constant current or constant voltage), temperature controlled is preferred because the various embodiments are intended to be used within the body. Control over the temperature of heating element 16 can advantageously avoid tissue damage caused by temperature. In addition, signal level changes in response to the heat dissipation characteristics of the environment in which heating element 16 is disposed will be maximized.

The anemometry circuitry shown in FIG. 2 includes balancing bridge circuit 28, controlled amplifier 30, and signal amplifier 32. Although other designs and configurations for the circuitry could be used, this simplified representation is included for ease of discussion. Bridge circuit 28 is comprised of heating element 16, a system controlled variable resistor 34 and two fixed resistors 36 and 38. Heating element 16 acts as a resistor within bridge circuit 28.

Bottom node 41 of bridge 28 is connected to ground (e.g. 0 volts). Thus, when a voltage is applied at top node 40 of bridge 28, current will flow through heating element 16, causing a dissipation of power. Due to the material and construction of heating element 16, the dissipated power is dissipated as heat. The heat will raise the temperature of heating element 16 such that the temperature change will cause a change in the resistance of heating element 16.

For the sake of simplicity, it is assumed that fixed resistors 36 and 38 have the same resistance value. Although this is not required, this assumption makes explanation of the anemometry circuitry easier to understand. As heating element 16 increases in temperature, the resistance of heating element 16 also increases, causing the voltage at first junction 42 (between heating element 16 and resistor 36) to increase.

Thus, if variable resistor 34 has a resistance value adjusted by the circuitry to be equal to that of heating element 16, then the voltage at second junction 44 (between fixed resistor 38 and variable resistor 34) will be the same as at first junction 42. When the voltages are equivalent, bridge circuit 28 is understood to be "balanced". Thus, once variable resistor 34 has been adjusted to have a resistance value equal to that of heating element 16, any changes to the resistance of heating element 16 (e.g., caused by changes in temperature) will cause the voltage at junction 42 to change in the direction of and roughly in proportion to the temperature change of heating element 16. Thus, the voltage at first junction 42 would be either higher or lower than the voltage at second junction 44.

Amplifier 30 is electrically coupled to bridge circuit 28 to sense the difference in voltage drop across heating element 16 and variable resistor 34 caused by the difference between the resistance of heating element 16 and the resistance of variable resistor 34. Amplifier 30 receives power, from positive Vsupply and is also coupled to ground. Amplifier 30 compares the voltages of positive input 46 and negative input 48. If positive input 46 is a higher voltage than negative input 48, the positive difference between input 46 and input 48 is amplified and output through line 50.

It is worth noting that no voltage higher than positive Vsupply will be seen at output 50. If negative input 48 is equal to or higher than positive input 46, then the voltage present at output 50 will be a low positive value (e.g., too low to cause significant heating of heating element 16). Amplifier 30 is able to compare the input voltages since positive input 46 is connected to second junction 44, and negative input 48 is connected to first junction 42. Output 50 of amplifier 30 is connected to top node 40 of bridge circuit 28.

Focusing now on the interaction between amplifier 30 and bridge circuit 28, it is assumed that bridge circuit 28 is initially in a balanced condition. Thus, the voltage applied to top node 40 of bridge circuit 28 by output 50 of amplifier 30 is low, and heating element 16 is not being heated. Also, the resistance of heating element 16 is equal to that of variable resistor 34.

If the anemometry circuitry system raises the resistance of variable resistor 34, the voltage at junction 44 will exceed the voltage at junction 42. This, in turn, creates a positive voltage difference between positive input 46 and negative input 48. This positive voltage difference causes output 50 to dramatically rise in voltage.

Output 50 is applied to top node 40 of bridge circuit 28, raising the current through heating element 16, which causes the power (e.g., heat) dissipated by heating element 16 to increase dramatically. The increase in heat dissipated by heating element 16 results in an increase in the temperature of heating element 16.

When the temperature of heating element 16 nearly reaches the temperature at which the resistance of heating element 16 is the same as that of variable resistor 34, the voltages at junctions 42 and 44 will be very close to equal. In addition, output 50 applied to top node 40 of bridge circuit 28 will begin to drop until an equilibrium is reached. Upon reaching this equilibrium, heating element 16 will be heated to a temperature that correlates to a resistance that is very close to that of variable resistor 34. With high amplification factors in amplifier 30, this resistance difference can be made to be negligible.

Since the resistance/temperature relationship of heating element 16 is known and heating element 16 now has the same resistance as variable resistor 34, the temperature of heating element 16 is also known. Thus, this interaction allows the temperature of heating element 16 to be set by adjusting the value of variable resistor 34 so long as positive Vsupply can supply enough voltage/current to top node 40 of bridge circuit 28 to sufficiently heat heating element 16 to the desired temperature. It is worth noting that the desired temperature is above ambient temperature of heating element 16 and that output 50 is at some intermediate voltage value between the maximum and minimum values for which amplifier 30 is configured when heating element 16 is heated above the ambient temperature.

Thus, output 50 is directly related to the heat transfer environment of heating element 16. If that environment carries heat away from heating element 16 rapidly, then output 50 will be a higher value than if that environment carries heat away more slowly.

It is expected that these changes in output 50 may be small. Thus, signal amplifier 32 is employed to increase the size of the change to a level suitable for an associated instrument (not shown) to sample, process, and display the measurements in a suitable manner. Signal amplifier 32 operates similarly to controlled amplifier 30. However, signal amplifier 32 is supplied with negative Vsupply, instead of power supply ground. Thus, output 56 may vary between the values of positive Vsupply and negative Vsupply in response to the voltage difference of inputs 52 and 54.

If positive input 52 is a higher voltage than negative input 54, then the positive difference between the two inputs is amplified, and the amplified voltage is presented at output 56. If positive input 52 is a lower voltage than negative input 54, then the negative difference between the two inputs is amplified, and the amplified negative voltage is presented at output

56. It is worth noting that the amplification factor for negative and positive differences is the same.

Negative input 54 is connected to wiper 58 of system controlled potentiometer 60. Potentiometer 60 is also connected to positive Vsupply and power supply ground such that, as wiper 58 is adjusted, the voltage at wiper 58 will vary between zero and the voltage of positive Vsupply.

Assuming that heating element 16 is maintained at a higher than ambient temperature, amplifier 32 behaves in the following manner. Since voltage output 50 is connected to positive input 52 of amplifier 32, input 52 is at some intermediate positive voltage level. The anemometry circuitry may then adjust wiper 58 such that negative input 54 is at or nearly at the same voltage as input 52. Thus, voltage output 56 of amplifier 32 will be approximately zero.

However, if heating element 16 is moved to an environment that transfers heat more rapidly, positive input 52 (from output 50) will exceed negative input 54 (from wiper 58), and output 56 of amplifier 32 will increase a multiple of the actual increase seen at input 52 due to an amplification factor of amplifier 32. If heating element 16 is moved to an environment that transfers heat less rapidly, positive input 52 will be less than negative input 54, and output 56 of amplifier 32 will have a negative value which is a multiple of the actual decrease seen at input 52.

Although anemometry circuitry is generally used to measure the flow velocity of fluid or gas, or, where the dimensions of the flow conduit are known or constant, to calculate flow rates, various embodiments described herein use the detected differences in the heat dissipation characteristics of different body tissues to determine injection depth and/or tissue type. It is worth noting that the embodiments disclosed herein should not be limited to measuring the heat dissipation characteristics of tissues since there are other materials within the body which are not generally considered tissues but will still have measurable heat dissipation characteristics. For instance, spinal fluid and amniotic fluid are not considered tissues but could have their respective heat dissipation characteristics measured to determine injection depth or material type.

Focusing now on exemplary heat dissipation characteristics of different materials, atheroma is a degenerative accumulation of lipid-containing plaque on the innermost layer of a wall of an artery. For heat dissipation purposes, atheroma is generally a waxy substance with no blood flow. If device 10 were inserted into a layer of atheroma, heating element 16 would only dissipate a negligible amount of heat.

Similarly, fat tissue does not have much blood flow, and therefore, heating element 16 inserted into fat tissue would experience a low heat dissipation rate. However, the same heating element 16 inserted into muscle tissue, which has substantial blood flow, would experience a high heat dissipation rate, and if heating element 16 were inserted into a moving blood stream, the heat dissipation rate experienced by heating element 16 would be extremely high.

FIGS. 3-6 demonstrate how device 10 with a single heating element 16 can be used to control the depth of penetration of needle 12 into the wall of a coronary artery to desired penetration depth 26. It is assumed that device 10 is inside a suitable catheter (not shown) at the desired location, that the catheter is a relatively good thermal insulator, that heating element 16 is being driven at a temperature above blood temperature, and that the anemometry circuitry which drives heating element 16 is connected to heating element 16 and properly configured.

Figure 3:
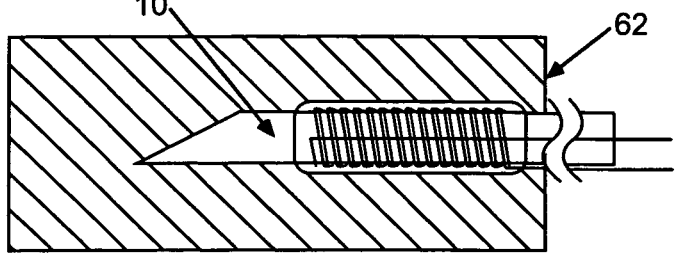
FIG. 3 shows the needle structure of FIG. 1 disposed within a blood stream.
Figure 6:
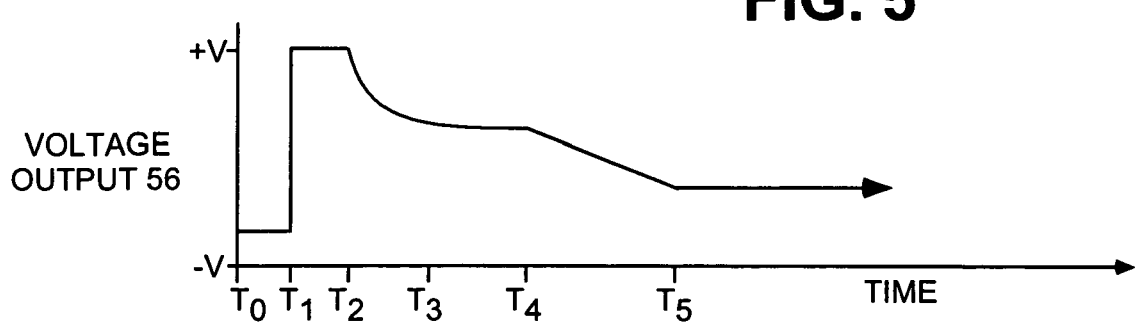
FIG. 6 is a graph which shows the voltage output of an embodiment as it varies over time during the insertion shown in FIGS. 3-5.

FIG. 6 shows a graph of voltage output 56 of amplifier 32 versus time. Before $T_1$, heating element 16 is inside the catheter (not shown). Since the catheter is assumed to be a relatively good thermal insulator, the drive voltage or current required to keep heating element 16 at a stable temperature is low. Thus, output 56 of amplifier 32 is very negative. At time $T_1$, device 10 is rapidly moved out of the catheter and into blood stream 62 of the artery (FIG. 3).

Blood stream 62 carries away heat at an extremely high rate, which cools heating element 16 mounted on device 10 rapidly. Thus, output 56 rises rapidly to a maximum value and remains at the maximum value until $T_2$, when heating element 16 has almost reached the set temperature (or resistance) again. At $T_3$, bridge circuit 28 reaches equilibrium with the new heat dissipation environment of blood stream 62. The line segment between $T_3$ and $T_4$ represents the new equilibrium level. This line segment is shown as a straight line for simplicity, but in reality, this line segment would have oscillations due to changes in the velocity of blood stream 62 relative to heating element 16 during the cardiac cycle.

Figure 4:
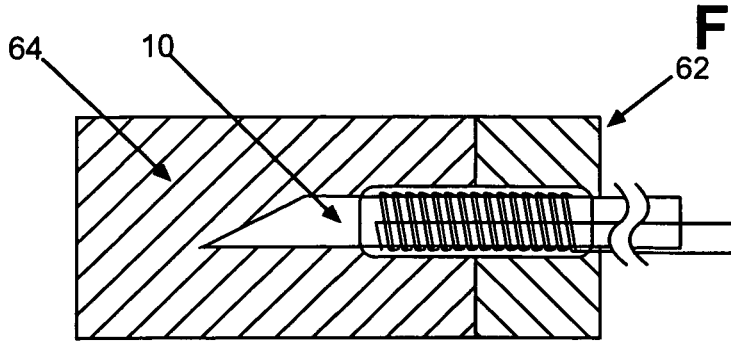
FIG. 4 shows the embodiment of FIG. 3 disposed partially in a vessel wall and partly in the blood stream.
Figure 5:
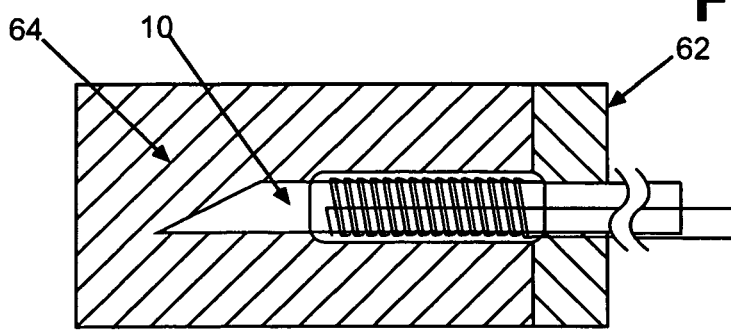
FIG. 5 shows the device of FIG. 4 disposed almost entirely within the vessel wall.

The line segment between $T_4$ and $T_5$ represents the smooth continuous insertion of heating element 16 into artery wall 64 (FIG. 4). Since artery wall 64 will be composed of atheroma, muscle tissue, connective tissue, and other surrounding tissues with low heat flow characteristics, artery wall 64 will be a better thermal insulator than blood stream 62. Thus, output 56 will change in a negative direction until heating element 16 is completely within artery wall 64 at $T_5$. FIG. 5 shows device 10 inserted into artery wall 64 to desired penetration depth 26.

As discussed above, the line segment between $T_4$ and $T_5$ is, shown as a straight line for simplicity, but in fact, the line segment will have the same cardiac cycle bumps as the line segment between $T_3$ and $T_4$. However, as more of heating element 16 is inserted into artery wall 64, the amplitude of these cardiac bumps will decrease until heating element 16 is no longer in blood stream 62.

One drawback of the single heating element design is that if needle 12 were inserted further into artery wall 64, there would be little change in output 56 to alert the user of the change in position. However, if second heating element 17 were mounted just proximal to first heating element 16 (FIG. 7), then desired penetration depth 26 could be more easily determined. Assuming heating elements 16 and 17 are constructed in the same manner, desired penetration depth 26 would be located when the greatest difference in outputs 56 of each of the respective heating elements was observed.

If needle 12 were further inserted into artery wall 64, output 56 of heating element 17 would decline toward the value of output 56 for heating element 16. Conversely, if needle 12 were withdrawn from artery wall 64, then output 56 of heating element 16 would increase toward the output 56 of heating element 17. Thus, multiple heating elements allow for monitoring the depth of penetration of needle 12 within relatively close limits relative to any tissue interface where the two interfacing tissues have sufficient difference in heat dissipation characteristics and thickness relative to the length of heating elements 16 and 17 to be detectable.

Figure 7:
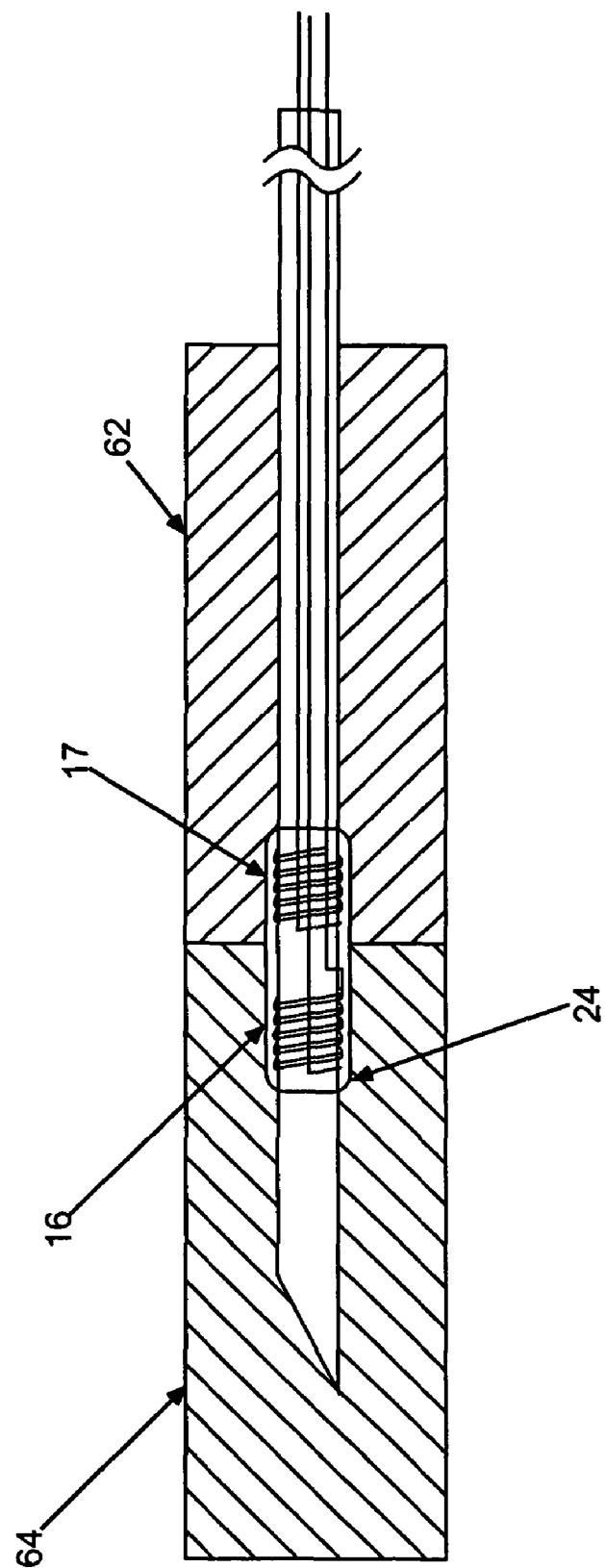
FIG. 7 shows an embodiment having multiple heating elements disposed on a needle such that one sensor is within the vessel wall and one sensor is disposed within the blood stream.

As shown in FIG. 7, multiple heating elements can be constructed within a single heating element assembly. For example, in the embodiment shown, heating element 16 and heating element 17 are both disposed in covering 24. In addition, only three electrical leads are required since each heating element has a separate bridge circuit 28 (not shown) connecting the heating element to ground (node 41 in FIG. 2). Thus, heating element 16 and heating element 17 share a lead to ground. In embodiments which use needle 12 as a conductive lead, needle 12 can be used as the ground connection for all heating elements.

The embodiments disclosed herein can be operated by much more complex and sophisticated circuitry and instrumentation to filter, process, and detect the differences in the heat dissipation characteristics of different tissue types. For example, the temperature of heating element 16 could be stepped in increments small enough to avoid saturating amplifier 30 toward or away from body temperature, using the rate of equilibrium establishment to differentiate tissue types or boundaries in a more rapid manner.

It is to be understood that even though numerous characteristics and advantages of various embodiments have been set forth in the foregoing description together with details of structure and function of the various embodiments, this disclosure is illustrative only. Changes may be made in detail, especially matters of structure and management of parts, without departing from the scope of the various embodiments as expressed by the broad general meaning of the terms of the appended claims.

I claim:

1. An apparatus comprising:
 a needle having dimensions suitable for insertion into a body, a distal portion suitable for insertion into tissue, a distal opening, and a lumen extending from a proximal end to the distal opening and in communication with the distal opening to allow a substance to be delivered through the lumen and out of the opening;
 a thermally conductive heating element coupled to the distal portion of the needle, the heating element comprising material whose electrical resistance changes in response to a change in temperature; and
 an interface to a balanced circuit having the heating element and a variable resistor as resistive circuit elements, wherein the balanced circuit measures a first differential resistance between the heating element and the variable resistor in response to a first condition and a second differential resistance in response to a second condition in circuitry to indicate a change of conditions related to a distance of penetration of the thermally conductive heating element into a tissue from a fluid boundary with the tissue, wherein the first condition comprises the distal portion of the needle penetrating a vessel wall first location and disposed in fluid, and the second condition comprises the distal portion of the needle extending through the fluid and disposed within tissue of a vessel wall second location.

2. The apparatus of claim 1, wherein the needle has an outer diameter between 0.009 inches and 0.134 inches.

3. The apparatus of claim 1, wherein the needle comprises a material of at least one of stainless steel and ceramic.

4. The apparatus of claim 1, wherein the needle is a rod.

5. The apparatus of claim 1, wherein the heating element comprises at least one of a wire, a film, and a thermistor material.

6. The apparatus of claim 1, wherein the heating element has a length which is approximately equal to or less than the thickness of a tissue in to which at least a portion of the needle is to be inserted.

7. The apparatus of claim 6, wherein the length of the heating element is between 0.010 inches and 0.400 inches.

8. The apparatus of claim 1, wherein the interface is an anemometry circuitry interface comprising:
 a first electrically conductive lead electrically coupled to a first end of the heating element; and
 a second electrically conductive lead electrically coupled to a second end of the heating element.

9. The apparatus of claim 1, wherein a portion of the needle comprises an electrically conductive material and wherein the interface comprises:
 an electrically conductive lead electrically coupled to a first end of the heating element, and
 the needle electrically coupled to a second end of the heating element.

10. The apparatus of claim 1 wherein the thermally conductive heating element is located distal to the distal opening.

11. The apparatus of claim 10, wherein the fluid is blood filling the vessel, and the second condition comprises a portion of the needle proximal to the heating element disposed within the fluid, and a distal end of the distal portion of the needle disposed within the tissue.

12. The apparatus of claim 1, further comprising a plurality of heating elements wherein the heating elements and the additional heating element are coupled along a length of the needle, and further comprising:
 anemometry circuitry separately coupled to each of selected heating elements of both the heating element and the plurality of heating elements such that the heat dissipation characteristics measured by the plurality of anemometry circuits can be used to determine at least one of injection depth and tissue type.

13. The apparatus of claim 1, further comprising anemometry circuitry electrically coupled to the heating element wherein the anemometry circuitry comprises a balanced circuit having a heating element and a variable resistor as resistive circuit elements, wherein the heating element comprises at least one of a wire, a film, and a thermistor material; and
 wherein the anemometry circuitry comprises:
  a circuit having the heating element and a variable resistor as resistive circuit elements; and
  an amplifier electrically coupled to the circuit
   to sense the difference in voltage drop across the heating element and the variable resistor caused by the difference between a first resistance of the heating element and a resistance of the variable resistor,
   to amplify the voltage difference, and
   to input the amplified voltage difference back to the circuit to cause a modification of a temperature of the heating element such that the heating element assumes a second resistance.

14. The apparatus of claim 1, wherein the distance of penetration is a distance through an inner surface of a vessel, from inside the vessel.

15. An apparatus comprising:
 a needle having dimensions suitable for insertion into a body, and having a distal end capable of puncturing skin;
 a thermally conductive heating element coupled to a portion of the needle adjacent to the distal end, the heating element comprising material whose electrical resistance changes in response to a change in temperature; and
 an interface to electrically couple an anemometry circuitry to the heating element, wherein the circuitry comprises a balanced circuit having the heating element and a variable resistor as resistive circuit elements to measure a first differential resistance between the heating element and the variable resistor in response to a first condition and a second differential resistance in response to a second condition, wherein the first condition comprises the distal end of the needle disposed in fluid, and the second condition comprises the distal portion of the needle disposed in the fluid and the distal end disposed within tissue.

16. The apparatus of claim 15, wherein the needle has an outer diameter between 0.009 inches and 0.134 inches, and wherein the distal end is sharpened.

17. The apparatus of claim 15, wherein the needle comprises a material of at least one of stainless steel and ceramic.

18. The apparatus of claim 15 wherein the needle has dimensions suitable for insertion into a tissue of the body and the balanced circuit is configured to measure a distance of penetration of the thermally conductive heating element into the tissue.

19. The apparatus of claim 15 wherein the thermally conductive heating element is located distal to the distal opening.

20. The apparatus of claim 15, wherein the heating element has a length which is approximately equal to or less than the thickness of a tissue in to which at least a portion of the needle is to be inserted.

21. The apparatus of claim 20, wherein the length of the heating element is between 0.010 inches and 0.400 inches.

22. The apparatus of claim 15, further comprising anemometry circuitry electrically coupled to the heating element wherein the circuitry comprises a balanced circuit having a heating element and a variable resistor as resistive circuit elements, wherein the heating element comprises at least one of a wire, a film, and a thermistor material.

23. The apparatus of claim 22, wherein the anemometry circuitry is electrically coupled to a first end of the heating element by a first electrically conductive lead and is electrically coupled to a second end of the heating element by a second electrically conductive lead.

24. The apparatus of claim 22, wherein a portion of the needle comprises an electrically conductive material and wherein the anemometry circuitry is electrically coupled to a first end of the heating element by an electrically conductive lead and is electrically coupled to a second end of the heating element by the needle.

25. The apparatus of claim 22, wherein the anemometry circuitry comprises:
   a circuit having the heating element and a variable resistor as resistive circuit elements; and
   an amplifier electrically coupled to the circuit
      to sense the difference in voltage drop across the heating element and the variable resistor caused by the difference between a first resistance of the heating element and a resistance of the variable resistor,
      to amplify the voltage difference, and
      to input the amplified voltage difference back to the circuit to cause a modification of a temperature of the heating element such that the heating element assumes a second resistance.

26. The apparatus of claim 22, further comprising a plurality of heating elements wherein the heating element and the plurality of heating elements are coupled along a length of the needle, and further comprising:
   anemometry circuitry separately coupled to each of selected heating elements of both the heating element and the plurality of heating elements such that the heat dissipation characteristics measured by the plurality of anemometry circuits can be used to determine at least one of injection depth and tissue type.

27. An apparatus comprising:
   a needle having dimensions suitable for insertion into a body, and having a distal end capable of puncturing skin;
   a thermally conductive heating element coupled to a portion of the needle adjacent to the distal end, the heating element comprising material whose electrical resistance changes in response to a change in temperature; and
   an interface electrically coupling an anemometry circuitry to the heating element, wherein the circuitry comprises a balanced circuit having the heating element and a variable resistor as resistive circuit elements, and wherein the anemometry circuitry comprises an amplifier electrically coupled to the circuit to sense the difference in voltage drop across the heating element and the variable resistor caused by the difference between a first resistance of the heating element and a resistance of the variable resistor.

* * * * *